United States Patent [19]

Yamamoto et al.

[11] Patent Number: 5,714,654
[45] Date of Patent: Feb. 3, 1998

[54] METHOD OF PRODUCING 1,1,1,3,3-PENTAFLUOROPROPANE AND/OR 1,1,3,3,3-PENTAFLUOROPROPENE

[75] Inventors: Akinori Yamamoto; Eiji Seki; Hirokazu Aoyama; Tatsuo Nakada, all of Settsu, Japan

[73] Assignee: Daikin Industries Ltd., Osaka, Japan

[21] Appl. No.: 549,816

[22] PCT Filed: May 30, 1994

[86] PCT No.: PCT/JP94/00865

§ 371 Date: Dec. 8, 1995

§ 102(e) Date: Dec. 8, 1995

[87] PCT Pub. No.: WO94/29251

PCT Pub. Date: Dec. 22, 1994

[30] Foreign Application Priority Data

Jun. 10, 1993 [JP] Japan .................. 5-165230
Dec. 29, 1993 [JP] Japan .................. 5-351633

[51] Int. Cl.⁶ .......................... C07C 19/08; C07C 21/18; C07C 17/354
[52] U.S. Cl. ................. 570/170; 570/124; 570/134; 570/135; 570/136; 570/175; 570/176
[58] Field of Search ................. 570/124, 134, 570/135, 136, 170, 175, 176

[56] References Cited

U.S. PATENT DOCUMENTS

| | | | |
|---|---|---|---|
| 4,902,839 | 2/1990 | Bielefeldt et al. | 570/175 |
| 4,954,666 | 9/1990 | Bielefeldt et al. | 570/132 |
| 5,068,473 | 11/1991 | Kellner et al. | 570/176 |
| 5,146,018 | 9/1992 | Kellner et al. | 570/156 |
| 5,268,122 | 12/1993 | Kao et al. | 570/134 |
| 5,504,265 | 4/1996 | Krespan et al. | 570/175 |
| 5,574,192 | 11/1996 | Van Der Puy et al. | 570/167 |

FOREIGN PATENT DOCUMENTS

| | | |
|---|---|---|
| 0 315 783 | 5/1989 | European Pat. Off. . |
| 1-146831 | 6/1989 | Japan . |
| 2-129131 | 5/1990 | Japan . |
| 4-503209 | 6/1992 | Japan . |

*Primary Examiner*—Shean C. Wu
*Attorney, Agent, or Firm*—Armstrong, Westerman, Hattori, McLeland & Naughton

[57] ABSTRACT

A method is proposed for producing 1,1,1,3,3-pentafluoropropane, in which 1,1,3,3,3-pentafluoropropene is reduced at a temperature between 40° C. and 300° C. by reacting it with hydrogen in a gas phase in the presence of a palladium catalyst. Further, a method is proposed for producing 1,1,1,3,3-pentafluoropropane and/or 1,1,3,3,3-pentafluoropropene, in which the raw material 2-chloro-1,1,3,3,3-pentafluoropropene is hydrogenated especially at a temperature between 30° C. and 450° C. in the presence of a catalyst composed of at least one metal selected from palladium, platinum and rhodium. Further, a method is proposed of producing 1,1,3,3,3-pentafluoropropene, in which 1,1,1,3,3-pentafluoro-2,3-dichloropropane is dechlorinated by using hydrogen in the presence of a metal oxide catalyst. Based on these production methods, 1,1,1,3,3-pentafluoropropane and/or 1,1,3,3,3-pentafluoropropene can thus be produced with high yield rates.

18 Claims, No Drawings

METHOD OF PRODUCING 1,1,1,3,3-PENTAFLUOROPROPANE AND/OR 1,1,3,3,3-PENTAFLUOROPROPENE

This application is a 371 of PCT/JP94/00865 filed May 30, 1994.

INDUSTRIAL USE

This invention relates to a method of producing a Useful compound of 1,1,1,3,3-pentafluoropropane which can be substituted for CFCs and HCFCs which are used as refrigerants, blowing agents and cleaning agents, and/or producing 1,1,3,3,3-pentafluoropropene which can be easily changed to 1,1,1,3,3-pentafluoropropane by hydrogenation and which is useful as an intermediate in the production of other fluorine-containing organic compounds as well as a monomer to produce high molecular compounds.

PRIOR ART

As a production method of 1,1,1,3,3-pentafluoropropane, it is known that 2,2,3-trichloro-1,1,1,3,3-pentafluoropropane is reduced by hydrogen by using a palladium catalyst (U.S. Pat. No. 2,942,036).

The known method, however, is not suitable for producing 1,1,1,3,3-pentafluoropane industrially because the yield of the product is low due to the formation of a large amount of 1,1,3,3,3-pentafluoropropene and 2-chloro- 1,1,3,3,3-pentafluoropropene as byproducts.

Another method is also known in which 1,1,3,3,3-pentafluoropropene is reduced by hydrogen at room temperature by using a palladium catalyst carried on alumina (Bull. Acad. Sol. USSR Div. Chem. Sci. (Eng. Transl.) 1312 (1960)).

In this known method, however, the yield of the target product of 1,1,1,3,3-pentafluoropropane is as low as about 70 percent.

1,1,3,3,3-pentafluoropropene is a useful compound which can be used as a raw material in producing various kinds of resins and as an intermediate in producing some medicines or agricultural chemicals, as well as a raw material of HFC blowing agents which do not destroy the ozone layer.

So far it is known that 1,1,3,3,3-pentafluoropropene can be synthesized by dehydrochlorination of 1,1,1,3,3-pentafluoro-3-chloropropane with a base (J. Am. Chem. Soc., 68 496(1946)).

In this known reaction, however, it is difficult to obtain the raw material and there are many problems in using the reaction industrially as a synthetic method of producing 1,1,3,3,3-pentafluoropropene.

Further, there is a known method of using decarboxylation of a potassium salt of α-hydroperfluoroisobythylate. In this method, however, it is difficult to obtain the raw material and it is difficult to use the decarboxylation reaction itself industrially (Synthesis of Fluoroorganic Compounds, I. L. Knunyants and G. G. Yakobson, Springer-Verlag, Berlin, Heidelberg, p.8 (1985)).

Besides, there is also a known method of using dehydroiodination of 3-iodo-1,1,1,3,3-pentafluoropropane, but again, it is difficult to obtain a large amount of the raw material at low cost (do., Synthesis of Fluoroorganic Compounds).

OBJECT OF INVENTION

It is an object of this invention to provide a method of producing 1,1,1,3,3-pentafluoropropane with a good yield by using 1,1,3,3,3-pentafluoropropene as a raw material.

It is another object of this invention to provide a method of producing 1,1,1,3,3-pentafluoropropane and/or 1,1,3,3,3-pentafluoropropene with a good yield by using 2-chloro-1,1,3,3,3-pentafluoropropene as a raw material.

It is a further object of this invention to provide a production method which is industrially feasible and easy to produce 1,1,3,3,3-pentafluoropropene by using 1,1,1,3,3-pentafluoro-2,3-dichloropropane as a raw material.

CONSTITUTION OF INVENTION

The inventors have studied methods of producing 1,1,1,3,3-pentafluoropropane by hydrogenating 1,1,3,3,3-pentafluoropropene in a gas phase. As a result of the study, the inventors found that though the usual hydrogenation of 1,1,3,3,3-pentafluoropropene at room temperature in the presence of a palladium catalyst results in a low conversion yield, a high reaction temperature improves the conversion yield and the object material Can be obtained with a high yield, thus achieving the first invention. Furthermore, the inventor found that when active carbon is used as a carrier of palladium catalyst, a selectivity of 100 percent can be attained.

That is, the first invention is a method of producing 1,1,1,3,3-pentafluoropropane with a high yield of 99 percent or more by hydrogenating 1,1,3,3,3-pentafluoropropene at a temperature of between 40° C. to 300° C. in the presence of a palladium catalyst.

In the method of the first invention, it is essential to use a temperature between 40° C. and 300° C. to realize the said object. A temperature below 40° C. lowers the conversion yield, while a temperature above 300° C. causes by-product formation and possible damage to the equipment to be used. The reaction temperature is preferably from 50° C. to 200° C.

As for the process of the gas phase reaction based on the first invention, such processes as the fixed bed vapor phase reaction and fluidized bed vapor phase reaction can be used.

A palladium catalyst to be used in the first invention can be used by being carried on a carrier composed of at least one selected from active carbon, silica gel, titanium oxide and zirconia, preferably being carried on active carbon.

The particle size of the carrier has little effect on the reaction, but it is preferably be from 0.1 to 100 mm.

As for the catalyst concentration on the carrier, a wide range from 0.05 to 10 wt. percent can be used, but a concentration from 0.5 to 5 wt. percent is recommended.

In the reduction reaction of 1,1,3,3,3-pentafluoropropene with hydrogen, the ratio of hydrogen to the raw material can be changed widely, but hydrogenation is usually carried out by using at least the stoichiometric amount of hydrogen. To the total mole of the starting material, however, a considerable excess moles of hydrogen of five or more times the stoiohiometrio amount can be used. The excess hydrogen can be reused after being recovered.

The reaction pressure is not restricted particularly. Though the reaction can be carried out under pressure, at a reduced pressure or at normal pressure, it is preferable to carry out the reaction under pressure or at normal pressure.

The contact time is usually from 0.1 to 300 seconds, preferably from 1 to 30 seconds.

The raw material 1,1,3,3,3-pentafluoropropene to be used in the reaction of the first invention can be obtained, for example, by dechlorinating 2,3-dichloro-1,1,1,3,3-pentafluoropropane with zinc metal under the reflux of ethanol. After the suspension of 1.5 equivalent parts of zinc metal to 2,3-dichloro-1,1,1,3,3-pentafluoropropane in ethanol was heated and refluxed, 1,1,3,3,3-pentafluoropropene could be obtained with a yield of 90 percent by dropping 2,3-dichloro-1,1,1,3,3-pentafluoropropane into the suspension.

Furthermore, after studying the processes of producing 1,1,1,3,3-pentafluoropropane and 1,1,3,3,3-pentafluoropropene, the inventor found a process in which the object materials can be obtained with high yields when 2-chloro-1,1,3,3,3-pentafluoropropene as a raw material is hydrogenated in the gas phase in the presence of a catalyst composed of a metal selected from palladium, platinum and rhodium, and thus completed the second invention.

That is, the second invention is a method of producing 1,1,1,3,3-pentafluoropropane and/or 1,1,3,3,3-pentafluoropropene with a high yield by hydrogenating the raw material 2-chloro-1,1,3,3,3-pentafluoropropene at a temperature especially from 30° C. to 450° C., in the presence of a catalyst composed of at least one metal selected from palladium, platinum and rhodium.

As for the process of the gas phase reaction based on the second invention, such processes as the fixed bed vapor phase reaction and fluidized bed vapor phase reaction can be used.

A catalyst composed of at least one metal selected from palladium, platinum and rhodium should preferably be carried on a carrier composed of at least one selected from active carbon, alumina, silica gel, titanium oxide, zirconia and others.

Though the particle size of the carrier has little effect on the reaction, it is preferably be from 0.1 to 100 mm.

As for the catalyst concentration on the carrier, though a wide range from 0.05 to 10 wt. percent can be used, a concentration from 0.5 to 5 wt. percent is usually recommended.

The reaction temperature is usually from 30° C. to 450° C., preferably from 70° C. to 400° C.

In the reduction reaction of 2-chloro-1,1,3,3,3-pentafluoropropene with hydrogen, the ratio of hydrogen to the raw material can be changed widely, but hydrogenation is usually carried out by using at least the stoichiometric amount of hydrogen. To the total mole of the starting material, however, a considerable excess moles of hydrogen of five or more times the stoichiometric amount can be used.

The reaction pressure is not restricted particularly. Though the reaction can be carried out under pressure, at a reduced pressure or at normal pressure, it is preferable to carry out the reaction under pressure or at normal pressure.

The contact time is usually from 0.1 to 300 seconds, preferably from 1 to 30 seconds.

The raw material 2-chloro-1,1,3,3,3-pentafluoropropene can be obtained with a good yield, for example, by dehydrochlorination of 2,2-dichloro-1,1,1,3,3-pentafluoropropane in an aqueous solution of alkaline compounds such as potassium hydroxide. The reaction temperature is preferably be from 0° to 100° C. The concentration of alkali should preferably be from 10 to 70%. The reaction pressure is not restricted particularly. Though the reaction can be carried out under pressure, at a reduced pressure or at normal pressure, it is preferable to carry out the reaction under pressure or at normal pressure.

1,1,1,3,3-pentafluoropropane can be quantitatively obtained by reacting 1,1,3,3,3-pentafluoropropene obtained in this reaction with a palladium catalyst in a gas phase (especially in the above-mentioned reaction of the first invention). In the reaction of the second invention, however, 1,1,1,3,3-pentafluoropropane can be formed directly from a starting material.

After studying processes of producing 1,1,3,3,3-pentafluoropropene effectively and at low cost, the inventors found a process in which 1,1,3,3,3-pentafluoropropene is derived with a high selectivity from 1,1,1,3,3-pentafluoro-2,3-dichloropropane which is available at low cost, resulting in the third invention.

That is, the third invention is a method of producing 1,1,3,3,3-pentafluoropropene by dechlorinating 1,1,1,3,3-pentafluoro-2,3-dichloropropane with hydrogen in the presence of a metal oxide catalyst.

In the third invention, the raw material 1,1,1,3,3-pentafluoro-2,3-dichloropropane can be easily obtained by fluorinating hexachloropropene with HF in the presence of antimony halide.

In the reductive dehalogenation of 1,1,1,3,3-pentafluoro-2,3-dichloropropane according to the third invention, the metal oxide to be used as a catalyst is preferably be an oxide of at least one metal selected from iron, chromium, cobalt, copper, nickel and manganese.

The metal oxide catalyst can be obtained by burning a metal hydroxide, which is precipitated by adding an alkali of aqueous ammonia or an alkali metal hydroxide in an ordinary way to an aqueous solution of a chloride, sulfate or nitrate of a metal such as chromium, iron, cobalt, copper, nickel and manganese. These metal oxide catalysts can be used alone, but a multiple oxide of several metals selected from the said metals and a mixture of several metal oxides can also be used in the reaction.

These metal oxide catalysts can be used in the pressed form of granules or pellets.

It is also acceptable for the catalyst to be carried on a carried which does not participate in the reaction, for example, at least one kind of carrier selected from active carbon, alumina, aluminum fluoride, silica gel and calcium fluoride. These metal oxides are allowed to have zero valence by pretreatment with hydrogen or reduction during the reaction.

As for the excess amount of hydrogen, though the reaction can be carried out when the mole ratio of hydrogen to the necessary raw material is 1 or more, in practice a ratio of 1.5 mole or more is preferable. Because excessive hydrogen reduces the contact time and reduces the conversion yield, a mole ratio of about 2 to 5 is used in practice.

The reaction temperature in the reductive dehalogenation is desirably from 200° C. to 400° C. and can be selected properly depending on the activity of the catalyst. As the velocity of the reaction is well-known to be increased by raising the reaction temperature, a high reaction temperature is needed when using a catalyst of low activity. But when the temperature is over 400° C., the ratio of C2 and C4 compounds, which are thought to be formed by the breaking and bonding of C—C bonds, is increased to lower the selectivity.

The contact time can be properly selected depending on the conversion yield set by the catalyst activity and the reaction temperature. Generally, when catalyst activity is low, the proper conversion yield can be set by extending the contact time.

Furthermore, this invention provides a method of producing 1,1,1,3,3-pentafluoropropane as the fourth invention, which is characterized by dechlorinating the said 1,1,1,3,3-pentafluoro-2,3-dichloropropane with hydrogen in the presence of a metal oxide catalyst and then reacting the obtained 1,1,3,3,3-pentafluoropropene with hydrogen in a gas phase in the presence of a palladium catalyst.

In the fourth invention, it is desirable to use the same metal oxide catalysts with their carriers, the amount of hydrogen to be used, and reaction temperature for dechlorination as those used in the above-mentioned third invention.

INDUSTRIAL POTENTIAL OF THE INVENTION

According to the first invention, 1,1,1,3,3-pentafluoropropane can be produced with a high yield because 1,1,3,3,3-pentafluoropropene is reduced by hydrogenation in a gas phase at a temperature between 40° C. and 300° C. in the presence of a palladium catalyst.

According to the second invention, 1,1,1,3,3-pentafluoropropane and/or 1,1,3,3,3-pentafluoropropene can be produced with a high yield because the raw material 2-chloro-1,1,3,3,3-pentafluoropropene is hydrogenated especially at a temperature between 30° C. and 450° C. in the presence of a catalyst composed of at least one metal selected from palladium, platinum and rhodium.

According to the third invention, 1,1,3,3,3-pentafluoropropene can be produced with a good selectivity because 1,1,1,3,3-pentafluoro-2,3-dichloropropane is dechlorinated with hydrogen in the presence of a metal oxide catalyst. The 1,1,3,3,3-pentafluoropropene can be changed to 1,1,1,3,3-pentafluoropropane by reaction with hydrogen in a gas phase in the presence of a palladium catalyst according to the fourth invention.

A product of this invention, 1,1,1,3,3-pentafluoropropane, is a useful compound which can be substituted for CFCs and HCFCs which are used as refrigerants, blowing agents and cleaning agents. Another product of 1,1,3,3,3-pentafluoropropene can be easily changed to 1,1,1,3,3-pentafluoropropane by hydrogenation and is a useful compound as an intermediate in the production of other fluorine-containing organic compounds as well as a monomer to produce high molecular compounds.

EXAMPLES

This invention is explained in more detail through the following examples.

EXAMPLE 1

A SUS-316 reactor tube 7 mm in inside diameter and 15 cm long was filled with 2.3 cc of a palladium catalyst carried on active carbon at 0.5% concentration. The reactor was heated to 100° C. in an electric furnace while passing nitrogen gas. After the temperature was reached, 1,1,3,3,3-pentafluoropropene was introduced into the reactor at the rate of 5.5 cc/min, together with hydrogen at the rate of 14.5 cc/min. The reaction temperature was kept at 100° C. The produced gas was washed with water and then analyzed by gas chromatography. The results are shown in Table 1.

EXAMPLE 2

The same reactor as used in Example 1 was filled with 2.3 cc of a palladium catalyst carried on active carbon at 0.5% concentration. The reactor was heated to 50° C. in an electric furnace while passing nitrogen gas. After the temperature was reached, 1,1,3,3,3-pentafluoropropene was introduced into the reactor at the rate of 5.5 cc/min, together with hydrogen at the rate of 14.5 cc/min. The reaction temperature was kept at 50° C. The produced gas was washed with water and then analyzed by gas chromatography. The results are shown in Table 1.

COMPARISON EXAMPLE

The same reactor as used in Example 1 was filled with 1.9 cc of a palladium catalyst carried on alumina at 0.5% concentration. After the reactor was kept at room temperature (23° C.) while passing nitrogen gas, 1,1,3,3,3-pentafluoropropene was introduced into the reactor at the rate of 5.5 cc/min, together with hydrogen at the rate of 14.5 cc/min. The produced gas was analyzed by gas chromatography after being washed with water. The target product 1,1,1,3,3-pentafluoropropane was obtained with a conversion yield of 75.3% and selectivity of 99.9%.

TABLE 1

| Example | Conversion (%) | Selectivity (%) |
| --- | --- | --- |
| Example 1 | 100 | 100 |
| Example 2 | 100 | 100 |
| Comparison example | 75.3 | 99.9 |

This result shows that the object compound can be obtained with high conversion yield and high selectivity when the reaction is carried out based on the method of the first invention.

EXAMPLE 3

A SUS-316 reactor tube 2 cm in inside diameter and 40 cm long was filled with 19 cc of a palladium catalyst carried on active carbon at 0.5% concentration. The reactor was heated to 200° C. in an electric furnace while passing nitrogen gas. After the temperature was reached, 2-chloro-1,1,3,3,3-pentafluoropropene, which had been gasified in advance, was introduced into the reactor at the rate of 32 cc/min, together with hydrogen at the rate of 128 cc/min. The reaction temperature was kept at 200° C. The produced gas was washed with water and dried with calcium chloride, then analyzed by gas chromatography. The results are shown in Table 2.

EXAMPLE 4

The same reactor as used in Example 3 was filled with 18 cc of a palladium catalyst carried on carbon pellets at 0.5% concentration. The reactor was heated to 250° C. in an electric furnace while passing nitrogen gas. After the temperature was reached, 2-chloro-1,1,3,3,3-pentafluoropropene, which had been gasified in advance, was introduced into the reactor at the rate of 22.8 cc/min, together with hydrogen at the rate of 136.8 cc/min. The reaction temperature was kept at 250° C. The produced gas was analyzed by gas chromatography after being washed with water and dried with calcium chloride. The results are shown in Table 2.

EXAMPLE 5

A SUS-316 reactor tube 7 mm in inside diameter and 15 cm long was filled with 1.9 cc of a palladium catalyst carried on carbon pellets at 3% concentration. The reactor was heated to 200° C. in an electric furnace while passing nitrogen gas. After the temperature was reached, 2-chloro-1,1,3,3,3-pentafluoropropene, which had been gasified in advance, was introduced into the reactor at the rate of 2.85 cc/min, together with hydrogen at the rate of 17.1 cc/min.

The reaction temperature was kept at 200° C. The produced gas was analyzed by gas chromatography after being washed with water and dried with calcium chloride. The results are shown in Table 2.

TABLE 2

| Example | Conversion (%) | Selectivity (%) 5FH | 245fa |
|---|---|---|---|
| Example 3 | 99.5 | 50.8 | 48.0 |
| Example 4 | 99.8 | 47.5 | 51.2 |
| Example 5 | 99.5 | 45.3 | 54.6 |

*In the table, 5FH and 245fa mean 1,1,3,3,3-pentafluoropropene and 1,1,1,3,3-pentafluoropropane, respectively.

The results show that the target product can be obtained with a high conversion yield and high selectivity when the reaction is carried out based on the method of the second invention.

EXAMPLE 6

120 g of $Cr(NO_3)_3.9H_2O$ was dissolved in 250 ml of water. The solution, being agitated with 200 ml of 28% aqueous solution of ammonium hydroxide, was added to 400 cc of heated water to precipitate the hydroxide. After being filtered, washed with pure water and dried, the precipitate was burnt at 450° C. for 5 hours to yield the powder of an oxide (chromium oxide). The powder was molded to a cylindrical form of 5 mm in diameter and 5 mm in height using a tapping mold machine.

10 g of the said chromium oxide powder was filled into a reactor tube made of Hastelloy C (Φ 20 mm×1000 mm). After the reactor was set at the reaction temperature, pretreatment was carried out in advance by passing hydrogen into the reactor at the rate of 200 ml/min for 3 hours. Then, 1,1,1,3,3-pentafluoro-2,3-dichloropropane was introduced into the reactor at the rate of 50 ml/min. The produced gas was analyzed by gas chromatography after being washed with water. The selectivity and conversion yield were calculated by multiplying areas of peaks in the gas chromatography analysis by correction factors determined separately. The results are shown in Table 3.

TABLE 3

| Reaction temperature | Conversion | Selectivity |
|---|---|---|
| 300° C. | 20% | 96% |
| 350° C. | 48% | 95% |
| 400° C. | 72% | 94% |

Though a main by-product was 1,1,1-tetrafluoro-3-chloropropene, it was proved that the target product (1,1,3,3,3-pentafluoropropene) can be obtained with high selectivity when the reaction is carried out based on the method of the third invention.

EXAMPLE 7

The reaction was carried out in the same way as Example 6 except that a multiple oxide of copper and chromium was used as the catalyst. The results are shown in Table 4.

TABLE 4

| Reaction temperature | Conversion | Selectivity |
|---|---|---|
| 300° C. | 35% | 87% |
| 350° C. | 52% | 85% |
| 400° C. | 84% | 82% |

Though a main product was 1,1,1,3-tetrafluoro-3-chloropropene, the target product was obtained with high selectivity also in this example.

EXAMPLE 8

The reaction was carried out in the same way as Example 6 except that an oxide of iron was used as the catalyst. The results are shown in Table 5.

TABLE 5

| Reaction temperature | Conversion | Selectivity |
|---|---|---|
| 300° C. | 18% | 89% |
| 350° C. | 33% | 86% |
| 400° C. | 68% | 78% |

Though a main byproduct was 1,1,1-tetrafluoro-3-chloropropene, the target product was obtained with high selectivity also in this example.

EXAMPLE 9

87 g of $Ni(NO_3)_2.6H_2O$ was dissolved in 250 ml of water. After adding 181 g of silica gel to the solution, the mixture was dried, then heated to 400° C. to yield nickel oxide. The oxide was molded to a cylindrical form of 5 mm in diameter and 5 mm in height using a tapping mold machine.

10 g of the said catalyst was filled into a reactor tube (Φ20 mm×1000 mm) made of Hastelloy C. After the reactor was set at the reaction temperature, pretreatment was carried out in advance by passing hydrogen into the reactor at the rate of 200 ml/min for 3 hours. Then, 1,1,1,3,3-pentafluoro-2,3-dichloropropane was introduced into the reactor at the rate of 50 ml/min. The produced gas was analyzed by gas chromatography after being washed with water. Selectivity and conversion yield were calculated by multiplying areas of peaks in the gas chromatography analysis by correction factors determined separately. The results are shown in Table 6.

TABLE 6

| Reaction temperature | Conversion | Selectivity |
|---|---|---|
| 300° C. | 21% | 92% |
| 350° C. | 43% | 85% |
| 400° C. | 72% | 82% |

Though a main by-product was 1,1,1-tetrafluoro-3-chloropropene, the target product was obtained with high selectivity also in this example.

EXAMPLE 10

120 g of $Cr(NO_3)_3.9H_2O$ was dissolved in 250 ml of water. After adding 181 g of silica gel to the solution, the mixture was dried, then heated to 400° C. to yield oxide. The product was molded to a cylindrical form of 5 mm in diameter and 5 mm in height using a tapping mold machine.

10 g of the said catalyst was filled into a reactor tube (Φ 20 mm×1000 mm) made of Hastelloy C. After the reactor was set at the reaction temperature, pretreatment was carried out in advance by passing hydrogen into the reactor at the rate of 200 ml/min for 3 hours. Then, 1,1,1,3,3-pentafluoro-2,3-dichloropropane was introduced into the reactor at the rate of 50 ml/min. The produced gas was analyzed by gas chromatography after being washed with water. Selectivity and conversion yield were calculated by multiplying areas of peaks in the gas chromatography analysis by correction factors determined separately. The results are shown in Table 7.

TABLE 7

| Reaction temperature | Conversion | Selectivity |
| --- | --- | --- |
| 300° C. | 20% | 98% |
| 350° C. | 46% | 96% |
| 400° C. | 74% | 95% |

Though a main byproduct was 1,1,1,3-tetrafluoro-3-chloropropene, the target product was obtained with high selectivity also in this example.

EXAMPLE 11

Potassium fluoride aqueous solution (5.4 moles) was added to calcium nitrate aqueous solution (2.7 moles). To the obtained slurry, copper nitrate (1 mole), nickel nitrate (1 mole) and chromium nitrate (1 mole) were added. Then, potassium hydroxide (0.1 mole) was added. The precipitated solid was filtered and dried, then heated to 400° C. to yield an oxide. The product was molded to a cylindrical form of 5 mm in diameter and 5 mm in height using a tapping mold machine.

10 g of the said catalyst was filled into a reactor tube (Φ 20 mm×1000 mm) made of Hastelloy C. After the reactor was set at the reaction temperature, pretreatment was carried out in advance by passing hydrogen into the reactor at the rate of 200 ml/min for 3 hours. Then, 1,1,1,3,3-pentafluoro-2,3-dichloropropane was introduced into the reactor at the rate of 50 ml/min. The produced gas was analyzed by gas chromatography after being washed with water. Selectivity and conversion yield were calculated by multiplying areas of peaks in the gas chromatography analysis by correction factors determined separately. The results are shown in Table 8.

TABLE 8

| Reaction temperature | Conversion | Selectivity |
| --- | --- | --- |
| 300° C. | 35% | 98% |
| 350° C. | 82% | 95% |
| 400° C. | 91% | 93% |

Though a main byproduct was 1,1,1,3-tetrafluoro-3-chloropropene, the target product was obtained with high selectivity also in this example.

We claim:

1. A method of producing 1,1,1,3,3-pentafluoropropane, which comprises reducing 1,1,3,3,3-pentafluoropropene by reacting it in the gas phase at a temperature between 40° and 300° C. with hydrogen in the presence of a palladium catalyst on an active carbon carrier.

2. A method according to claim 1, wherein the concentration of the palladium on the carrier is between 0.05 and 10% by weight of the carrier.

3. A method according to claim 1, wherein the reduction is carried out using at least the stoichiometric amount of hydrogen to 1,1,3,3,3-pentafluoropropene.

4. A method of producing 1,1,1,3,3-pentafluoropropane, which comprises reducing 1,1,3,3,3-pentafluoropropene by reacting it in the gas phase at a temperature between 40° and 300° C. with hydrogen in the presence of a palladium catalyst carried on a silica gel, titanium oxide or zirconia carrier.

5. A method according to claim 4, wherein the concentration of the palladium on the carrier is between 0.05 and 10% by weight of the carrier.

6. A method according to claim 4, wherein the reduction is carried out using at least the stoichiometric mount of hydrogen to 1,1,3,3,3-pentafluoropropene.

7. A method of producing 1,1,1,3,3-pentafluoropropane and 1,1,3,3,3-pentafluoropropene, which comprises reducing 2-chloro-1,1,3,3,3-pentafluoropropene by reacting it in the gas phase with hydrogen at a temperature between 30° and 450° C. in the presence of a catalyst comprising at least one metal selected from the group consisting of palladium, platinum and rhodium.

8. A method according to claim 7, wherein the catalyst is supported on at least one carrier selected from the group consisting of active carbon, alumina, silica gel, titanium oxide and zirconia.

9. A method according to claim 8, wherein the concentration of the catalyst on the carrier is between 0.05 and 10% by weight of the carrier.

10. A method according to claim 7, wherein the reduction is carried out using at least the stoichiometric amount of hydrogen to 2-chloro-1,1,3,3,3-pentafluoropropene.

11. A method of producing 1,1,1,3,3-pentafluoropropane, which comprises dechlorinating 1,1,1,3,3-pentafluoro-2,3-dichloropropane with hydrogen in the presence of a metal oxide catalyst at a temperature between 200° and 400° C.

12. A method according to claim 11, wherein the metal oxide is an oxide of at least one metal selected from the group consisting of iron, chromium, cobalt, copper, nickel and manganese.

13. A method according to claim 12, wherein the metal oxide catalyst is supported on at least one carrier selected from the group consisting of active carbon, alumina, aluminum fluoride calcium fluoride and silica gel.

14. A method according to claim 11, wherein the dechlorination reacting is carried out using at least the stoichiometric amount of hydrogen to 1,1,1,3,3-pentafluoro-2,3-dichloropropane.

15. A method of producing 1,1,1,3,3-pentafluoropropane, which comprises dechlorinating 1,1,1,3,3-pentafluoro-2,3-dichloropropane with hydrogen in the presence of a metal oxide catalyst at a temperature between 200° and 400° C. to form 1,1,3,3,3-pentafluoropropene, and then reducing the 1,1,3,3,3-pentafluoropropene in the gas phase with hydrogen at a temperature between 40° and 300° C. in the presence of a palladium catalyst.

16. A method according to claim 15, wherein the metal oxide is an oxide of at least one metal selected from the group consisting of iron, chromium, cobalt, copper, nickel and manganese.

17. A method according to claim 15, wherein the metal oxide catalyst is carried on at least one carrier selected from the group consisting of active carbon, alumina, aluminum fluoride, calcium fluoride and silica gel.

18. A method according to claim 15, wherein the dechlorination reaction is carried out using at least the stoichiometric amount of hydrogen to 1,1,1,3,3-pentafluoro-2,3-dichloropropane.

* * * * *